United States Patent [19]

Choksi

[11] Patent Number: 4,717,403
[45] Date of Patent: Jan. 5, 1988

[54] LIQUID TRAP FOR MEDICAL APPLICATION

[75] Inventor: Pradip V. Choksi, Northridge, Calif.

[73] Assignee: SpaceLabs, Inc., Bothell, Wash.

[21] Appl. No.: 853,077

[22] Filed: Apr. 17, 1986

[51] Int. Cl.[4] ............................................. B01D 45/12
[52] U.S. Cl. ...................................... 55/429; 55/431; 55/459 R; 55/DIG. 35; 128/205.27
[58] Field of Search ................. 55/218, 215, 429, 431, 55/439, 458, 459 R, DIG. 35; 128/205.27, 205.12, 204.16, 205.29

[56] References Cited

U.S. PATENT DOCUMENTS

| | | | |
|---|---|---|---|
| 375,463 | 12/1887 | Stratton | 55/459 R X |
| 441,995 | 12/1890 | Wheeler | 55/459 R X |
| 498,557 | 5/1893 | Lee | 55/458 X |
| 1,103,549 | 7/1914 | Spencer | 55/459 R X |
| 1,170,438 | 2/1916 | Fahrney | 55/429 X |
| 1,856,685 | 5/1932 | Anderson | 55/458 X |
| 2,121,538 | 6/1938 | Farmer | 55/429 X |
| 2,692,026 | 10/1954 | Frantz | 55/218 |
| 2,725,115 | 11/1955 | Miller | 55/429 X |
| 3,488,927 | 1/1970 | Jepsen et al. | 55/431 X |
| 3,543,325 | 12/1970 | Hamrick | 55/429 X |
| 3,788,044 | 1/1974 | McNeil | 55/218 X |
| 3,802,570 | 4/1974 | Dehne | 55/459 R X |
| 4,350,510 | 9/1982 | Hamada et al. | 55/459 R X |
| 4,430,994 | 2/1984 | Clawson et al. | 128/205.12 X |
| 4,506,523 | 3/1986 | DiCarlo et al. | 55/459 R X |
| 4,579,568 | 4/1986 | Ricciardelli et al. | 55/204 X |
| 4,592,368 | 6/1986 | Ricciardelli et al. | 128/205.27 X |

FOREIGN PATENT DOCUMENTS 2036606  7/1980  United Kingdom ............ 55/459 R

Primary Examiner—Kathleen J. Prunner
Attorney, Agent, or Firm—Seed and Berry

[57] ABSTRACT

A water trap for use in a capnographic sampling line is disclosed. It includes a main body, a liquid collection chamber in communication with ambient atmosphere through a first channel, a cylindrically shaped separation chamber which communicates at a first end with ambient atmosphere through the top of the main body and at its end opposite the first end with the collection chamber, and a sampling gas input channel in communication with ambient atmosphere and which extends into the separation chamber tangentially to the interior wall thereof.

3 Claims, 10 Drawing Figures

LIQUID TRAP FOR MEDICAL APPLICATION

BACKGROUND OF THE INVENTION

The present invention relates to medical carbon dioxide in the exhaled breath of a patient (known as capnography). More particularly, the present invention relates to water traps used with such devices.

The measurement of a patient's carbon dioxide level is an important parameter in the diagnosis of a patient's pulmonary function. Capnography is done on a continuous basis and the values of carbon dioxide level are displayed as a curve on a CRT.

Measurement of carbon dioxide gas level is done by aspirating a continuous stream of gas from the patient's exhalation line and feeding it into an infra red sensor. The flow rate of the sample stream is usually 200 ml/min or less. In order to minimize dampening of the signal, the internal volume of the sampling line is kept as small as possible (about 2 ml.). The inside diameter of the sampling line is often 1 mm (0.40 inches) or smaller.

The exhaled gases leave the patient at 99° Fahrenheit (F) and virtually 100 per cent relative humidity. The gas cools in the sampling line (the line is at room temperature usually around 70°) and moisture condenses. It is important to remove this moisture from the line and collect it in a container for easy disposal.

SUMMARY OF THE INVENTION

The present invention relates to an apparatus for separating liquid such as condensed moisture from gas in a patient's sampled air stream. The apparatus, or water trap, includes a main body having a liquid collection chamber and a separation chamber. The separation chamber communicates at a first end through the top of the main body with ambient atmosphere and at its opposite end with the collection chamber. A sample gas input channel is tangentially coupled to the separation chamber at the separation chamber's interior wall.

In the preferred embodiment, the apparatus includes an upper main body portion which contains the separation chamber and a cup detachably mounted to the upper body portion to form the collection chamber.

DETAILED DESCRIPTION OF THE DRAWINGS

Figure 1:
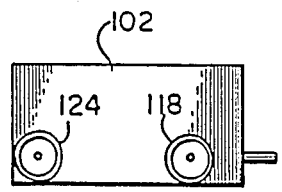
FIG. 1 is a top planar view of a prior art water trap device used in capnography.
Figure 2:
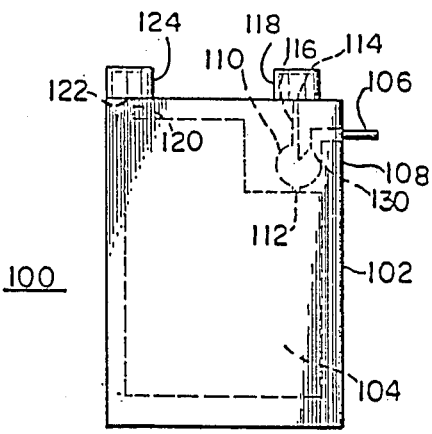
FIG. 2 is a planar elevational view of the water trap of FIG. 1.

Prior art water traps for use with capnography are provided by a number of companies including Biochem and Puritan-Bennett. FIGS. 1 and 2 show a water trap approach used in the prior art designated generally 100. It comprises a housing 102 having a moisture collection chamber 104. A flexible sampling line (made of vinyl, nylon, Nafion etc.) fits over and is coupled to a sample gas input tube 106 which enters the housing through a hole in a side wall 108 in a horizontal direction. The input tube allows communication between the interior of the connected sampling line and a smaller chamber 110 within the housing which is positioned below the place where the input tube enters the housing. The smaller chamber 110 is generally round in cross section and is coupled to the larger collection chamber 104 at the bottom of hole 112 and to an exit port 114 in the top of the housing 102 by a gradually narrowing pathway 116. The exit port 114 is surrounded on the top of the housing 102 by a latex rubber sleeve 118 adapted to make sealing contact with a line coupled to a vacuum source at the sensor instrument.

The chamber 104 has an opening 120 coupled to a second port 122 on the top of the housing 102 which is also surrounded by a latex rubber sleeve 124 adapted to receive a line coupled to a vacuum source.

The device 100 of FIGS. 1 and 2 works as follows: gas from the sampling tube coupled to the brass input tube 106 is pulled into the housing 102 by the vacuum on the line coupled to port 114. The gas and condensed moisture present in the gas sample are pulled through the round smaller chamber 110. The moisture being heavier than the gas tends to settle at the bottom of the chamber 110 and be pulled through hole 112 into the collection chamber 104 by the partial vacuum present there due to coupling of port 122 to the vacuum source (not shown).

The gas in the gas stream on the other hand is lighter than the condensed moisture and it tends to rise and be pulled through the port 114 by the vacuum source coupled thereto. Gravity acts to separate the moisture from the gas in the chamber 110. However, before separation of the gas and moisture can occur, the sampling gas and condensed moisture, still mixed, are pulled down along path 130 toward the chamber 110 and then through the chamber 110. Separation then occurs because the gas rises vertically through the gradually narrowing pathway 116 and the liquid falls through the hole 112 into the collection chamber 104.

In the prior art device the collection chamber 104 which acts as a cup for the condensed moisture separated from the sampling gas in an integral part of the overall device 100. It cannot be separated from the device and emptied. To empty the chamber, the entire device must be disconnected from the sampling line interrupting the gas sampling process. Emptying then requires the use of a syringe to force the liquid out of the collection chamber 104.

Figure 3:
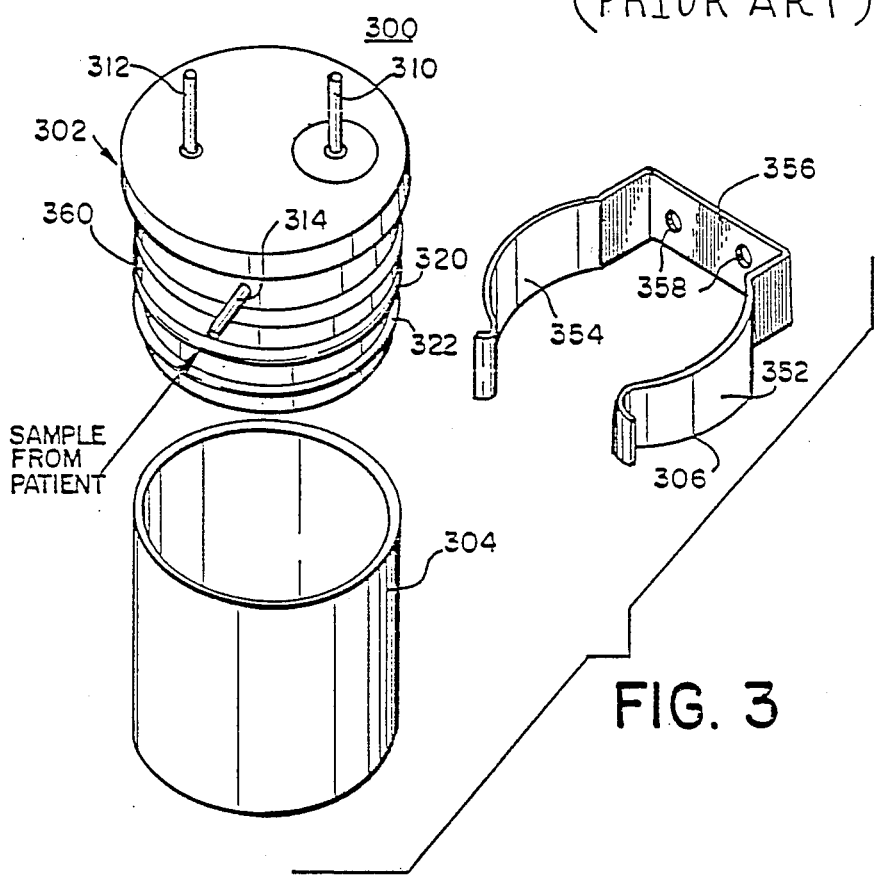
FIG. 3 is an exploded view of the preferred embodiment water trap of the present invention.

FIG. 3 is an exploded assembly drawing of the water trap assembly of the present invention designated generally 300. It comprises a moisture separator means 302 and a disposable cup 304 for collection of the moisture after separation.

Means 306 for holding the assembly to an external frame or the sensing instrument is also provided.

Referring now to FIGS. 4, 5, 6, and 8, the separation means 302 comprises an upper cylindrical main body 402 with central axis 404 and an annular wall 406 integrally formed with the bottom of the main body and extending therefrom. The annular wall 406 defines a large central void 408 open to the ambient atmosphere at the bottom. The axis 404 is coaxial with the central axis of the annular wall 406.

The main body comprises a cylindrical separation chamber 410 having a central axis 412 substantially parallel with the axis 404 and spaced apart therefrom. The separation chamber has an elongated main portion 414 with a constant diameter throughout which opens to a larger diameter shorter portion 416 which opens to the ambient atmosphere at the top of the main body. The elongated main portion 414 at its end opposite portion 416 opens to a quickly narrowing portion 418 which ends in a small diameter hole 419 which opens into the void 408 at the bottom of the main body 402.

The main body further comprises a second cylindrical channel 420 with an axis 422 parallel to that of axis 404 and 412. It opens at one end into said void 408 and at its opposite end through a short tapering region 424 to ambient atmosphere at the top of the main body.

The annular wall 406 has a pair of outer parallel and spaced apart circumferential grooves 430 and 432. Main body 402 has an indented centrally located circumferential outer annular region 434 formed between parallel and spaced apart annular ridges 360 and 362.

Figure 6:
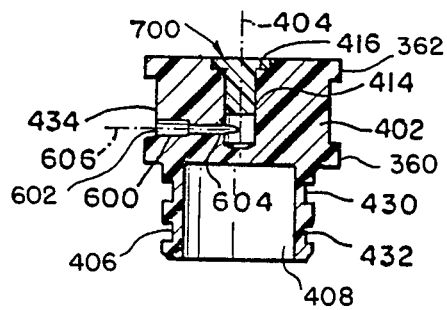
FIG. 6 is another cross sectional view of the water separation mechanism of FIG. 4 taken along the lines and arrows 6—6 in FIG. 5.

FIG. 6 is an elevational-cross sectional view of the separation means 302 taken through the axis 404 and showing a horizontal channel 600 in the main body extending from the annular region 434 where the horizontal channel 600 opens to ambient atmosphere into the main portion 414 of the separation chamber 410. The channel 600 comprises a first larger diameter portion 602 with one end at the annular region 434 and a second smaller diameter portion 604 extending into the main portion 414 tangential to the curved wall thereof and reaching the center 404 of the main body 402. The axis 606 of the horizontal channel 600 is substantially perpendicular to the axis of the separation chamber 410.

Figure 7:
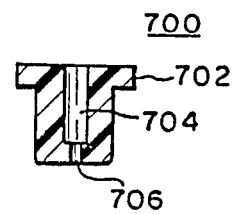
FIG. 7 is an elevational cross sectional view of a plug for use with the water separation mechanism of FIGS. 3-6.
Figure 5A:
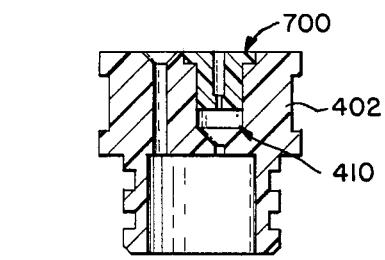
FIG. 5A is a cross sectional view of the water separation mechanism of FIG. 4 taken along the lines and arrows 5—5 in FIG. 4 and including a cross sectional view of the plug of FIG. 7 shown positioned within the water separation mechanism.

FIG. 7 shows cylindrical rubber plug 700 with circular cross section and adapted for frictional fit within the separation chamber 410. See FIG. 5A. It extends down into the main portion 414 of the separation chamber 410 but is prevented from reaching the bottom because of larger diameter shorter portion 702 which fits within the larger diameter shorter portion 416 of the separation chamber. The plug has a center channel 704 of first larger diameter which runs from its top to near the bottom where it narrows to a small diameter hole 706 which opens out through the bottom of the plug. When inserted in the separation chamber, the bottom of the plug is above the entry of the horizontal channel 600 into the separation channel.

The plug 700 is inserted into the separation chamber 410, and brass tubes 310, 312 and 314 are inserted into the plug channel 704, the second cylindrical channel 420 and the horizontal channel 600, respectively. In the preferred embodiment, the larger portion of the plug channel, the horizontal channel and the main portion of the second cylindrical channel in the main body are substantially the same and accept the same size brass tube. Rubber O-rings 320 and 322 are snapped into position within circumferential grooves 430 and 432. The cylindrically shaped disposable cup 304 is then pushed into place over the annular wall and over the O-rings which form an air tight seal.

As a holder for the assembly a metal bracket 306 with curved spring like arms 352 and 354 are connected at one end by a straight section 356 having a pair of holes 358 therethrough. The arms are separated slightly to receive the top of the cup just below the lower annular ridge 360 of the main body and then released to close around the cup and assembly. The holes are used to attach the bracket to a convenient external frame, wall or the sensing instrument itself.

Figure 4:
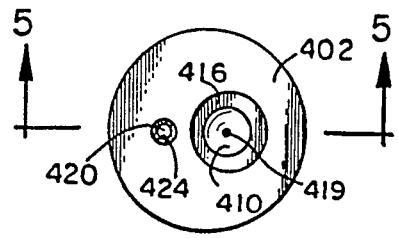
FIG. 4 is a top planar view of the water separation mechanism of the water trap of FIG. 3.
Figure 5:
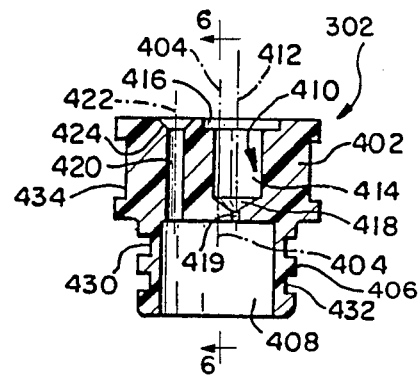
FIG. 5 is a cross sectional view of the water separation mechanism of FIG. 4 taken along the lines and arrows 5—5 in FIG. 4.
Figure 3A:
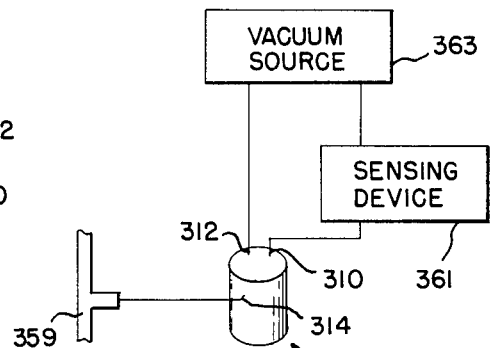
FIG. 3A is a schematic representation of the coupling of the present invention water trap with a vacuum source and the patient's air stream.
Figure 8:
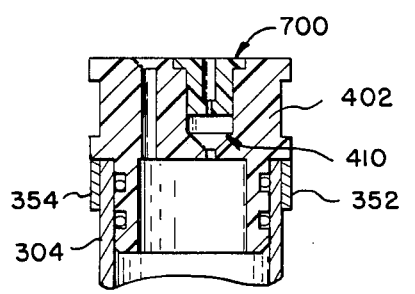
FIG. 8 is a cross-sectional view of the water trap in its assembled condition.

Referring now to FIGS. 3A, 4 and 7, sampled gas is drawn from the air stream 359 of the patient through the brass tube 314 in the horizontal channel where it enters the separation chamber 410 below the plug tangentially to the curved wall of the main portion of the separation chamber. The sampled gas flows circularly within the separation chamber 410 causing a centrifugal separation of the gas and condensed moisture. The gas being lighter rises and is pulled by the vacuum through the channel 706 in plug 700 and then out the brass tube 310 and through the remainder of the sampling line into the sensing device 361.

The moisture being heavier falls to the bottom of the separation chamber 410 and is pulled through the bottom hole 419 of the separation chamber 410 by the partial vacuum present in the void enclosed by the cup and created by connecting the brass tube 312 in the second channel 420 to a vacuum source 363. The moisture collects in the cup and when it is desired to empty the cup it is pulled downwardly from the main body and emptied. A new cup is slipped into place. This is done without interruption of the sampling process.

In the present invention, the separation process begins immediately upon entry of the sampled gas into the separation chamber. It is not necessary to pull the gas and condensed moisture downwardly together before passing through a separation chamber as in the prior art. The circular movement of the sampled gas in the separation chamber of the present invention provides additional time for the separation process to take place before the gas is pulled off.

What is claimed is:

1. An apparatus for separating liquid from gas in a sampled airstream from a patient, comprising:
    a moisture collection cup; and
    moisture separation means mounted on said moisture collection cup, said moisture separation means having:
    (a) a cylindrical separation chamber having a volume that is substantially smaller than the volume of said collection cup;
    (b) an input channel tangentially open to the interior of said separation chamber;
    (c) a gas outlet port positioned above said input channel;
    (d) a moisture outlet channel positioned below said input channel and extending between said separation chamber and moisture collection cup, said separation chamber being devoid of any physical structure between said input channel and gas outlet part; and
    (e) a channel extending into the upper portion of said moisture collection cup.

2. The apparatus of claim 1, further comprising:

an annular wall portion integrally formed with said moisture separation means and extending downwardly therefrom to receive said moisture collection cup, said annular wall portion comprising at least one outer circumferential groove, said apparatus further comprising:

an O-ring positioned in said at least one groove to form a fluid seal with said moisture separation cup.

3. The apparatus of claim 1 wherein said apparatus further comprises a plug disposed to fit within the upper end of said separation chamber and extending only partway down said separation chamber, said plug comprising a channel therethrough to form said gas outlet port.

* * * * *

UNITED STATES PATENT AND TRADEMARK OFFICE
CERTIFICATE OF CORRECTION

PATENT NO. : 4,717,403
DATED : January 5, 1988
INVENTOR(S) : Pradip V. Choksi

It is certified that error appears in the above—identified patent and that said Letters Patent is hereby corrected as shown below:

Claim 1, line 19, delete "part" and substitute therefor --port--.

Signed and Sealed this

Twenty-fourth Day of May, 1988

Attest:

DONALD J. QUIGG

Attesting Officer

Commissioner of Patents and Trademarks